(12) United States Patent
Amato

(10) Patent No.: US 8,535,063 B1
(45) Date of Patent: *Sep. 17, 2013

(54) CRANIOFACIAL ANATOMIC SIMULATOR WITH CEPHALOMETER

(75) Inventor: Cyrus J. Amato, Califon, NJ (US)

(73) Assignee: Amato Craniofacial Engineering, LLC, Califon, NJ (US)

(*) Notice: Subject to any disclaimer, the term of this patent is extended or adjusted under 35 U.S.C. 154(b) by 231 days.

This patent is subject to a terminal disclaimer.

(21) Appl. No.: 13/025,540

(22) Filed: Feb. 11, 2011

Related U.S. Application Data

(63) Continuation-in-part of application No. 12/004,542, filed on Dec. 20, 2007, now Pat. No. 7,909,610.

(60) Provisional application No. 60/871,441, filed on Dec. 21, 2006, provisional application No. 60/885,570, filed on Jan. 18, 2007, provisional application No. 60/899,441, filed on Feb. 6, 2007.

(51) Int. Cl.
*G09B 23/28* (2006.01)

(52) U.S. Cl.
USPC ............................................... 434/270

(58) Field of Classification Search
USPC .................. 434/262, 263, 264, 267, 270, 274
See application file for complete search history.

(56) References Cited

U.S. PATENT DOCUMENTS

| 1,586,739 | A | 2/1921 | Hanau |
|---|---|---|---|
| 3,802,096 | A | 4/1974 | Matern |
| 4,200,996 | A | 5/1980 | Richards |
| 4,541,807 | A | 9/1985 | Rolfs |
| 4,708,836 | A | 11/1987 | Gain et al. |
| 4,948,373 | A | 8/1990 | Engels |
| 5,090,910 | A | 2/1992 | Narlo |
| 5,320,535 | A | 6/1994 | Min |
| 5,342,202 | A | 8/1994 | Deshayes |
| 5,720,612 | A | 2/1998 | Shih |
| 6,112,109 | A | 8/2000 | D'Urso |
| 6,582,232 | B1 | 6/2003 | Ney |
| 6,701,174 | B1 | 3/2004 | Krause et al. |
| 6,790,043 | B2 | 9/2004 | Aboud |
| 6,978,188 | B1 | 12/2005 | Christensen |
| 7,731,499 | B2 | 6/2010 | Sze et al. |
| 2005/0043835 | A1 | 2/2005 | Christensen |
| 2005/0133955 | A1 | 6/2005 | Christensen |
| 2008/0070212 | A1 | 3/2008 | Haber |

*Primary Examiner* — Kurt Fernstrom
(74) *Attorney, Agent, or Firm* — Siegmar Silber, Esq.

(57) ABSTRACT

A craniofacial anatomic simulator with cephalometer is disclosed and omnidirectional osteogenesis is provided as an example thereof. The craniofacial anatomic simulator (CAS) includes an articulator in which a stereolithographic medical model is mounted. The medical model hereof is modified for this purpose so that the mandibular portion is mounted together with the craniomaxillary portion in a manner which simulates the excursive movement of the temporomandibular joint and the masseteric sling providing both rotational and translational motion. The cephalometer consists of three digital calipers that provide locational data—height, depth and lateral position for any point on the stereolithographic model.

14 Claims, 4 Drawing Sheets

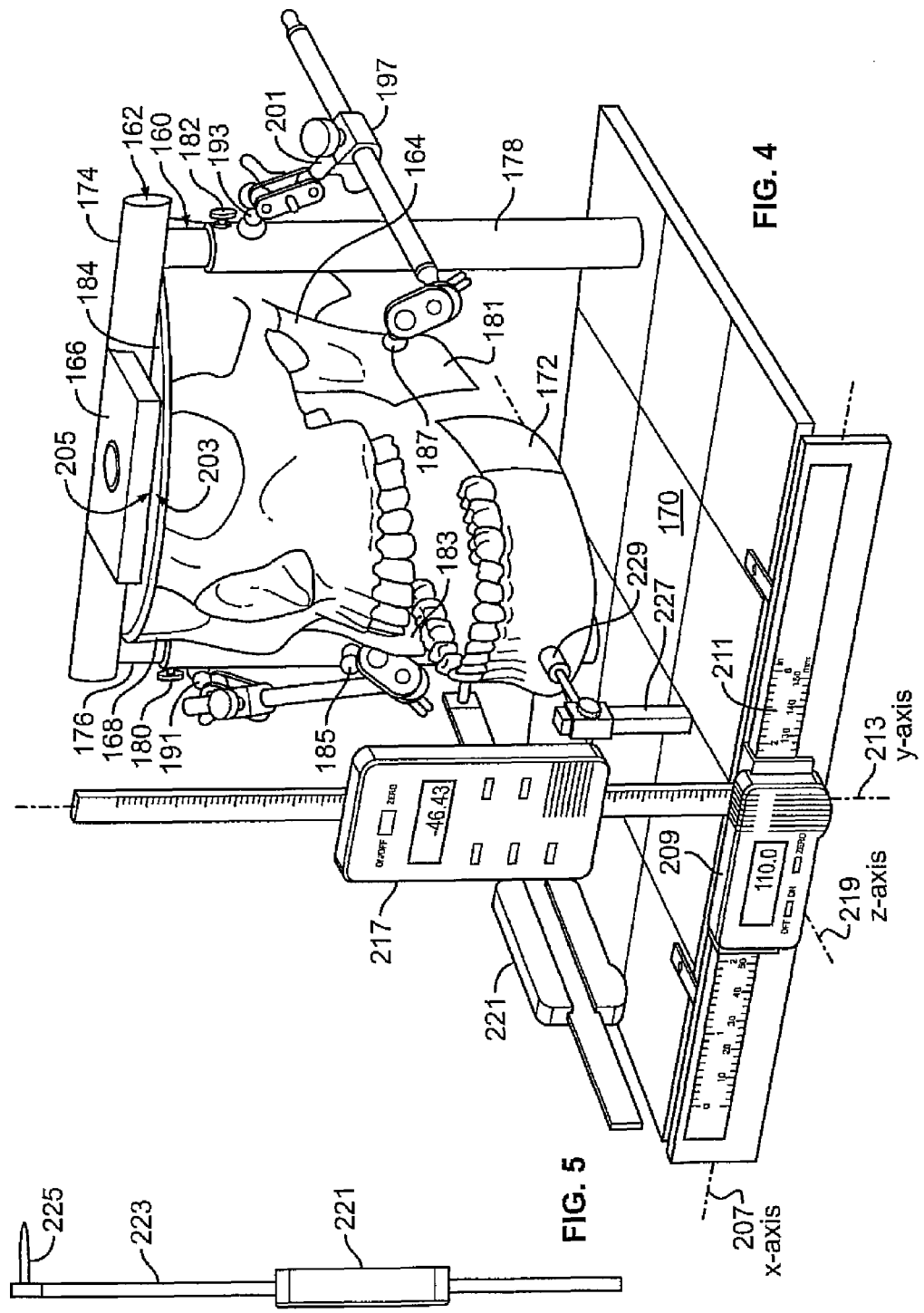

CRANIOFACIAL ANATOMIC SIMULATOR WITH CEPHALOMETER

CROSS REFERENCE TO RELATED APPLICATIONS

This application is a Continuation-in-Part of U.S. patent application Ser. No. 12/004,542, filed Dec. 20, 2007, entitled Computer-Aided System of Orthopedic Surgery, which, in turn, is a non-provisional of Provisional Application 60/871,441, filed Dec. 21, 2006, of Provisional Application 60/885,570, filed Jan. 18, 2007; and of Provisional Application 60/899,441 filed Feb. 6, 2007, said applications incorporated herein by reference.

BACKGROUND OF THE INVENTION

1. Field of Invention

The present invention relates to methods, devices, and computer generated models for a system of orthopedic surgery and more particularly for surgical employment of distraction osteogenesis using intra-oral omnidirectional distraction devices. This invention is implemented using medical imaging; medical modelling; computer-aided design and manufacturing; a novel craniofacial anatomic simulator with cephalometer; and, a precision docking mechanism that allows omnidirectional positioning of skeletal segments.

2. Description of the Related Art

In the past, computerization for surgical preplanning purposes has provided stereolithographic models of the anatomic site. These are three-dimensional models constructed using digitized information from scanning devices such as laser and acoustic reflection apparatus and various types of transmission apparatus including X-ray, magnetic resonance imaging (MRI), positron emission (PET or SPECT) as well as ultrasonic radiation.

Upon data being captured by scanning a series of spaced parallel planes, the scans are combinable by computed-tomographic (CT) techniques to construct a three dimensional projection of the scan in the form of a medical model such as a stereolithographic representation. Anatomical modeling using CT-scan data is well known and is widely accepted in pre-operative planning, rehearsal of surgical procedures, and the manufacture of prosthetic devices.

U.S. Pat. No. 6,112,109 of D'urso and U.S. Patent Application Publication 2005/0133955 both describe the use of CT-scan data for constructing prosthetic devices that are custom-fit to provide a better relationship between the remaining healthy bone and the orthopedic implant.

To implement the inventor's system of orthopedic surgery several heretofore unknown devices needed to be developed. A craniofacial anatomic surgical simulator is described, infra, for mounting and working the stereolithographic model. As background to this development, Krause et al. in U.S. Pat. No. 6,701,174 comment that in the complex area of bone distraction surgery "it is difficult, if not impossible, to make accurate surgical plans based solely on a limited number of two-dimensional renderings of bone geometry. This is because of the complex and inherently three-dimensional nature of bone deformities as well as of fixator geometry. Furthermore, two-dimensional depictions of surgical plans may not accurately portray the complexities involved in accessing the target positions of the osteotome and fixator pins surrounding the operated bone. Lack of three-dimensional modeling of these geometric complexities makes it difficult to accurately mount the fixator on the patient according to the presurgical plan".

The computer-assisted preplanning of Krause et al. made an early attempt to resolve this long-felt need through the use of a Taylor Spatial Frame—a collection of fixator struts and associated software; however, they found that the apparatus did not provide visual feedback on how the fixator frame and bone fragments should be moved over time.

As further background to the surgical simulator hereof, in the medical literature Cheung et al. In a 2007 article entitled, *Vector Guidance Splint for Internal Maxillary Distraction* (*JL Oral Maxillofacial Surgery*, pp. 1852 et seq.) reports using a Hanau Engineering Articulator, developed in the 1920's.

Taking dental articulators as the forebears of the Craniofacial Anatomic Simulator hereof leads one to view the articulator patent art starting with Hanau, U.S. Pat. No. 1,586,739 and leading patents to Tradowsky, U.S. Pat. No. 4,365,955; El Hadary, U.S. Pat. No. 5,073,109; Federici, U.S. Pat. No. 5,533,896; and Shih, U.S. Pat. No. 5,720,612. None of these devices fulfill the simulation requirements of the disclosure at hand.

SUMMARY

This disclosure describes a craniofacial anatomic simulator (CAS) for mounting a medical model such as a stereolithographic medical model. The framework of the CAS includes a fixed base and a pair of columns arising therefrom, which columns are adjustable to raise and lower a mounting plate on which the craniomaxillary portion of the medical model is mounted. The CAS also provides fixtures to mount the mandibular portion within the glenoid fossae and simulates the temperomandibular joint. The CAS facilitates the formation of pre-operative intra-oral devices and custom-made surgical guides required for a broad range of maxillofacial surgery.

The description of the preferred embodiments, infra, describes two models of the CAS which differ in the manner in which segmented portions of the medical model are held in place. Both describe mounting mandibular portions with three degrees of freedom. In the first embodiment this is accomplished with a movable base for mandibular mounting and in the second embodiment manipulators or "helping hands" are used in place thereof. It is further noted that the medical model is specific to the application at hand in that the truncated upper portion is replaced with a cranial mounting plate. Also, mounting nodes or connectors are placed about the medical model and the CAS framework to facilitate management of the medical model.

The CAS is constructed to enhance the measurement of cephalometric points by having digital calipers mounted on the fixed base. Additionally the stereolithographic model may be indexed within the CAS framework by having a computer generated midline reproduced on the cranial mounting plate of a model and matched to a similar midline of the upper mounting plate. Other details of the construct are described in the specification which follows.

OBJECTS AND FEATURES OF THE INVENTION

It is an object of the present invention to provide for pre-fitting or custom fabrication of internal devices for omnidirectional distraction, such as, for craniofacial surgery intra-oral distractors, docking bars, and modified occlusal splints.

It is another object of the present invention to provide a medical model, such as a computed tomographic (CT) generated stereolithographic facial skeleton, to optimize planning and preparation phase of craniofacial surgery.

It is yet another object of the present invention to provide a computer-aided system of surgery whereby through simulation information is gained as to anatomic variables, including the contour and surface mapping of the bone, the quality of the bone, and the location of neurovascular structures.

It is a further object of the present invention to provide in the pre-planning phase the most favorable osteotomy and ostectomy design and the analysis of possible anatomical interferences upon segmental movement.

It is yet another object of the present invention to provide a medical model suitable for mounting in an craniofacial anatomic surgical simulator therefor and facilitating the pre-fitting of internal devices.

It is a feature of the present invention that the craniofacial anatomic simulator hereof provides a mounting arrangement for a stereolithographic model wherein the truncated craniomaxillary portion and the mandibular portion are combined with a temporomandibular joint accurately simulating that of the patient.

It is yet another feature of the craniofacial anatomic simulator that the model temporomandibular joint allows simulation of excursive movement with translational and rotational components thereby enhancing surgical planning.

It is another feature of the present invention that the omnidirectional distraction with the anatomically contoured fixation plates prevents the difficulties of prior intra-oral devices which resulted in the undesired rotation of the maxilla.

Other objects and features of the invention will become apparent upon review of the drawings and the detailed description.

BRIEF DESCRIPTION OF THE DRAWINGS

The invention is described in more detail below with reference to the embodiments shown in the drawing in which like elements are labeled similarly.

FIG. 4 is a perspective view of the craniofacial anatomic simulator of this invention as shown in FIG. 3 but with the cephalometer added to the base; and, FIG. 5 is a top elevational view of the offset head of the depth digital caliper of the cephalometer.

DESCRIPTION OF THE PREFERRED EMBODIMENTS

This disclosure describes a new system of orthopaedic surgery, which changes present-day craniofacial procedures and is applicable to all forms of orthognathic surgery and dental and prosthetic procedures. As the simulator has particular application to distraction osteogenesis, in the description which follows distraction osteogenesis is used as an exemplary case. However, it should be borne in mind that by working with the craniofacial anatomic simulator of this invention, the ability of the surgeon to visualize the endpoint of the surgery—whether or not the procedure includes distraction osteogenesis—and to plan and detail the pathway to reach the endpoint is greatly enhanced hereby.

Surgical Preplanning

Figure 1:
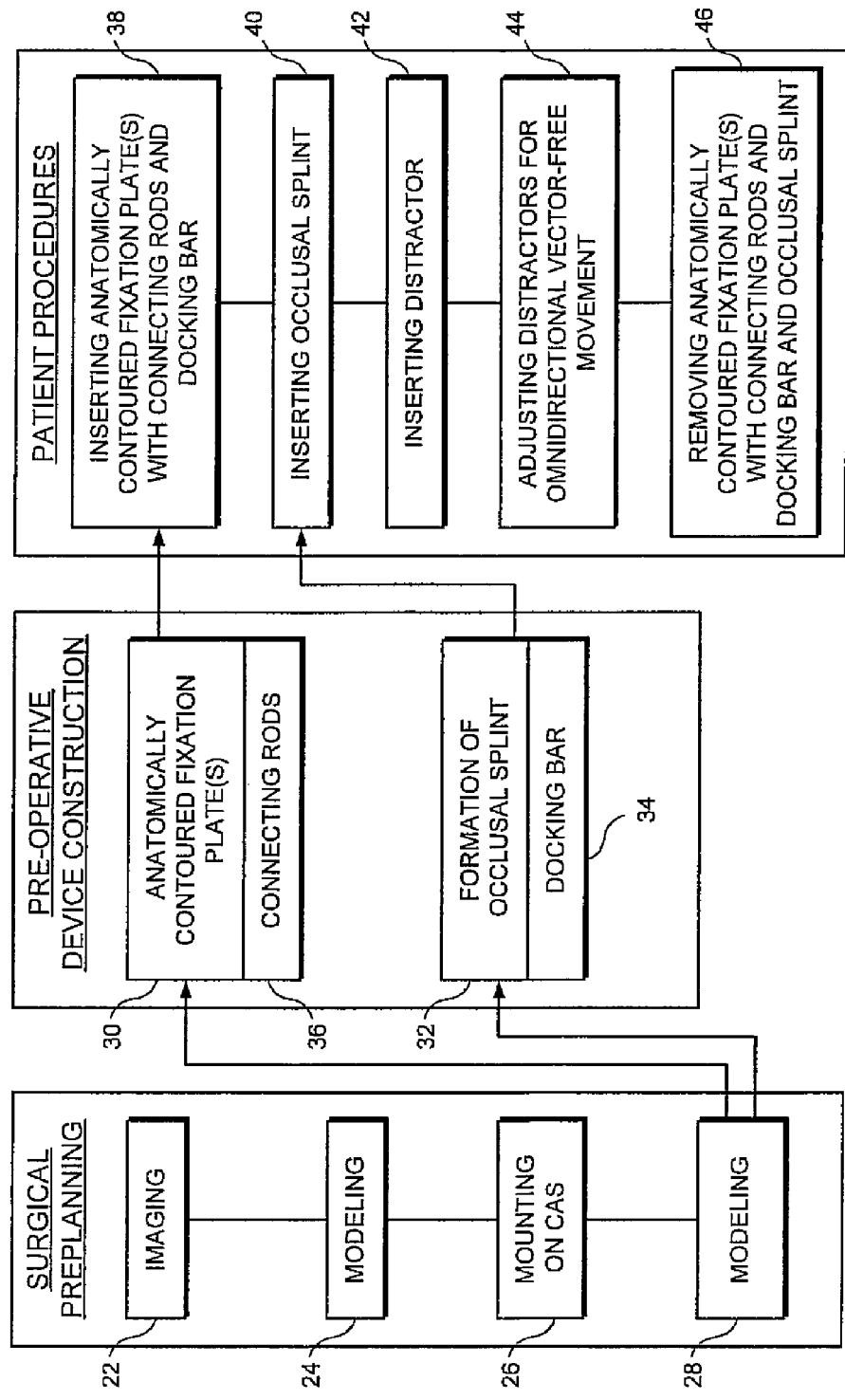
FIG. 1 is a schematic diagram of the new system of orthopedic surgery for which the craniofacial anatomic simulator is designed.

Referring to the schematic diagram of the system FIG. 1, a general overview of the new system of orthopedic surgery is now provided. Three principal divisions are apparent, namely, (1) surgical preplanning; (2) pre-operative device construction; and, (3) patient procedures.

Upon initializing the process, an IMAGING 22 of the patient is first undertaken. The IMAGING 22 step may obtain digitized data from scans of magnetic resonance imaging (MRI), X-ray, computed tomography (CT), ultrasound, laser interferometry or position emission technique (PET). From the collected data, accurate anatomic information as to the bone formation and bone malformation is available.

A medical model, preferably stereolithographic, is formed using MODELING 24 techniques presently extant. Typical of the available modeling techniques are those described in a Christensen, U.S. Patent Application Publication 2005/0133955 for custom prosthesis development. In preparation for the mounting of the model on the craniofacial anatomic surgical simulator which follows, the segments of the stereolithographic model are carefully evaluated.

The inventor's craniofacial anatomic simulator, described in detail herebelow, is now used to mount the parts of the stereolithographic model in the pre-operative positions thereof. The MOUNTING ON CAS 26 process is key to the extreme accuracy of the omnidirectional distraction. The MOUNTING ON CAS 26 process provides the facility for accurately forming the docking bar and the surface mapping required for the anatomically contoured fixation plates and the process does so without the need for vector determination or vector guides.

The mounted stereolithographic medical model also provides, during surgical preplanning, for the SIMULATING 28 phase. Here any osteotomy required and the incisions for installing the custom-fitted fixation plates are preplanned. Upon receipt of the customized contoured anchor from the laboratory, the casting is fitted to the model and, with the docking bar in place, the day-to-day distraction movement and adjustment is planned.

Pre-Operative Device Construction

Using omnidirectional distraction osteogenesis as an example, the surgeon, either alone or with the support team, forms a wax model for lost-wax casting of ANATOMICALLY CONTOURED FIXATION PLATES device 30. In the example described below, the medical model, being an accurate representation of the cranial skeletal structure, custom fits the ANATOMICALLY CONTOURED FIXATION PLATES 30 so as to follow the surface map of the bone contours at the site of installation. In this manner, the device is pre-operatively precision fitted to the patient and, unlike some prior art intra-oral devices, does not require bending at the time of installation. Besides the preciseness of custom-fitting and the removal of the bending requirement, the ANATOMICALLY CONTOURED FIXATION PLATES 30 are rigid devices which eliminate vector requirements, including vector alignment and vector guides.

Again using omnidirectional distraction osteogenesis as an example, the surgeon either alone or with the support team, places all the segments of the stereolithographic model in the post-operative position and forms an OCCLUSAL SPLINT/DOCKING BAR ARMATURE 32. With the segments of the model assembled on the CAS in the final position to be attained, the preforming of the DOCKING BAR 34 and designing and forming of the CONNECTING RODS 36 completes the pre-operative device construction. These devices enable the surgical procedure in which full distraction in all directions becomes feasible.

Patient Procedures

Referring again to FIG. 1, the operative steps are now described. First, the step of inserting the devices fabricated pre-operatively is completed. The INSERTING ANATOMICALLY CONTOURED FIXATION PLATE(S) WITH CONNECTING RODS AND DOCKING BAR 38 is accomplished with the ends of the fixation plates anchoring the plates by wrapping around and undercutting the bones at the installation sites. The occlusal splint upon which the docking bar 34 was formed is inserted at INSERTING OCCLUSAL SPLINT 40.

With this accomplished, a distractor, such as a Dynaform distractor (as manufactured by Stryker Leibinger BmbH & Co., Freiburg, Germany) is employed, and emplaced on the docking bar at INSTALLING DISTRACTOR 42.

With the device installation completed, what remains is ADJUSTING DISTRACTORS FOR OMNIDIRECTIONAL VECTOR-FREE MOVEMENT 44 and REMOVING ANATOMICALLY CONTOURED FIXATION PLATE(S) WITH CONNECTING RODS AND DOCKING BAR AND OCCLUSAL SPLINT 46.

Craniofacial Anatomic Simulator

Figure 2:
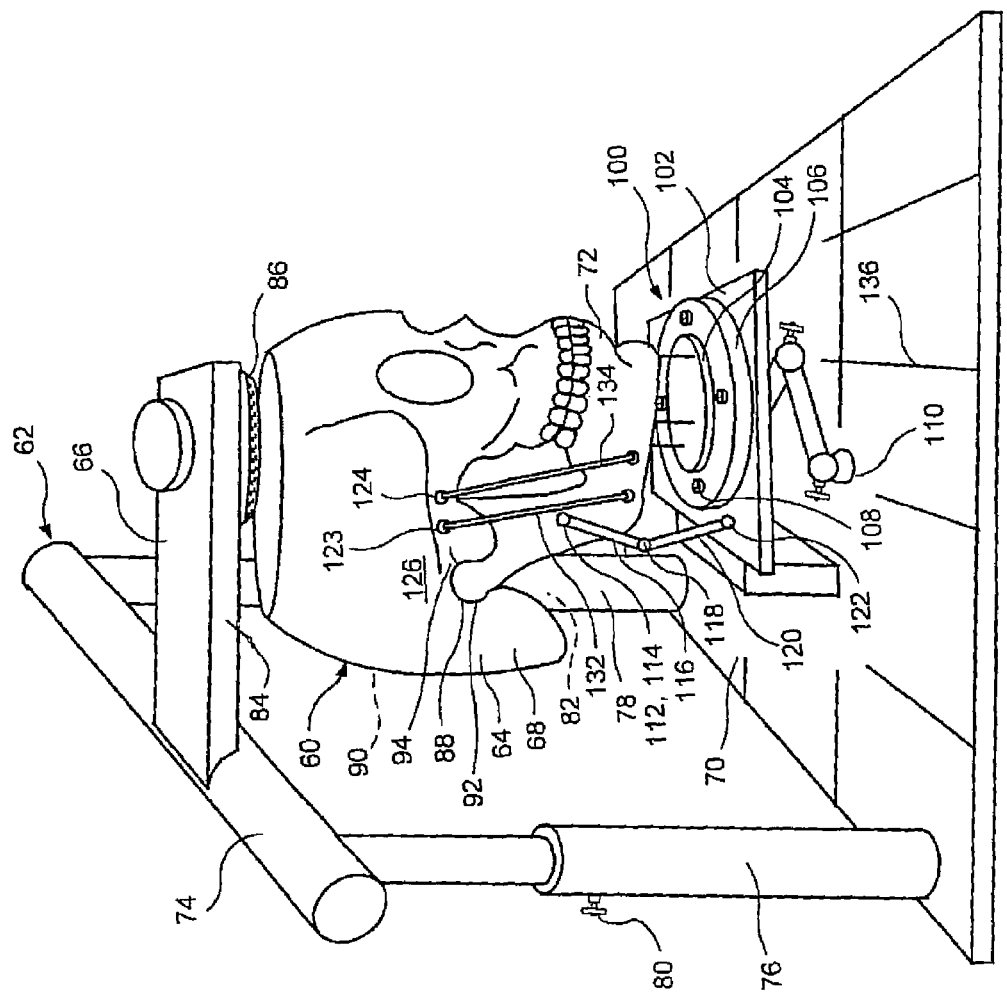
FIG. 2 is a perspective view of the first embodiment of the craniofacial anatomic simulator of this invention having a uniquely positionable mandibular mounting arrangement.

Referring now to FIG. 2, the craniofacial anatomic surgical simulator (CAS) is now described. The CAS is referred to generally by the reference designator 60 and provides a framework 62 for accommodating the stereolith model 64. The framework 62 is constructed with an upper mounting plate 66 for attaching the craniomaxillary portion 68 of the stereolithographic model 64 and a base mounting plate 70 for attaching the mandibular portion 72 of the stereolith model 64.

The framework 62 of the CAS 60 further comprises a crossbar or strut 74 to which the upper mounting plate 66 is connected. While in the present embodiment the strut 74 upper mounting plate 66 is fixed, it is within the contemplation of the present invention that this connection could swivel for right-to-left adjustment or be hinged for forward/back adjustment. The framework 62 of the CAS 60 further comprises adjustable posts or retaining elements 80 and 82 that maintain the upper mounting plate 66 at the selected elevation.

The medical model 64 consisting of the craniomaxillary portion 68 and the mandible or mandibular portion 72 is adapted for mounting on the CAS 60. The craniomaxillary portion 68 is modified for the purpose of the above-described surgery by having the uppermost cranial portion removed and replaced by a cranial attachment plate 84 which is mounted to the upper mounting plate 70 by an adhesive layer 86.

A simulated temporomandibular joint (TMJ) 88 and 90 is constructed to attach the mandible or mandibular portion between the base 70 and the craniomaxillary portion 68. As the stereolithographic model 64 does not replicate the soft tissue component of the TMJ 88 and 90, the simulation of the glenoid fossae 92 and the soft tissue therewithin is provided by a silicone liner or a soft dental liner or reline 94, such as COE-SOFT Resilient Dental Liner manufactured by GC America, Inc., Alsip, Ill. 60803 or equivalent. In further simulation of the TMJ 88 and 90, upper pegs 123 and 124 are inserted in the zygomatic arch 126 and lower pegs 128 and 130 are placed in the mandible 72 with elastics 132 and 134 therebetween. The angle of the elastics 132 and 134 mimic the masseteric sling and as is described hereinbelow provides simulation of the excursive movement of the mandible previously not experienced in craniofacial anatomic simulators.

The mandible 72 is also attached through a mandibular mounting mechanism 100 to the base mounting plate 70. The mounting mechanism 100 is constructed with a mandibular base plate 102 and intermediate plates 104 and 106. In the embodiment shown, plate 106 is attached to mandibular base plate 102 with three positioning screws 108 enabling the removal and remounting of the mandible 72 without losing the original location or orientation.

The mandibular mounting mechanism 100 is attached to the base 70 of the CAS 60 with two posts (not shown) and three universal movement lock joints 110. During simulated surgery, this mounting arrangement enables the movement of the mandible 72 vis-á-vis the craniomaxillary portion into the desired post-operative position.

When the CAS 60 is used to simulate mandibular ramus surgery, it is necessary to configure the device so that the proximal segment of the mandibular ramus is fixed. To accomplish this, a ramus pin 112 is disposed on both sides of the stereolith model 64 and a ramus pin lock joint 114, similar to lock joint 110, is secured thereto. Depending from lock joint 114 is upper guide rod 116, which, in turn, is secured to intermediate lock joint 118 and to lower guide rod 120. The lower guide rod 120 is secured to mandibular base plate 102 through base plate lock joint 122. With this structure in place, the mandible 72 relation to the craniomaxillary portion 68 is adjusted by a change in elevation at posts 76 and 78 being locked in place at clamps 80 and 82 and by unlocking the previously described lock joints sliding and rotating the segments to the desired position and locking the joints.

The temporomandibular joint TMJ 88 and 90, the soft tissue 94 and elastics 132 and 134 are constructed to simulate the excursive movement of the TMJ by providing a forward and downward sliding motion or translation and mandibular rotation. The structure also simulates mandibular movement by balancing lateral excursions having one side providing rotation and the opposite side providing translation.

Figure 3:
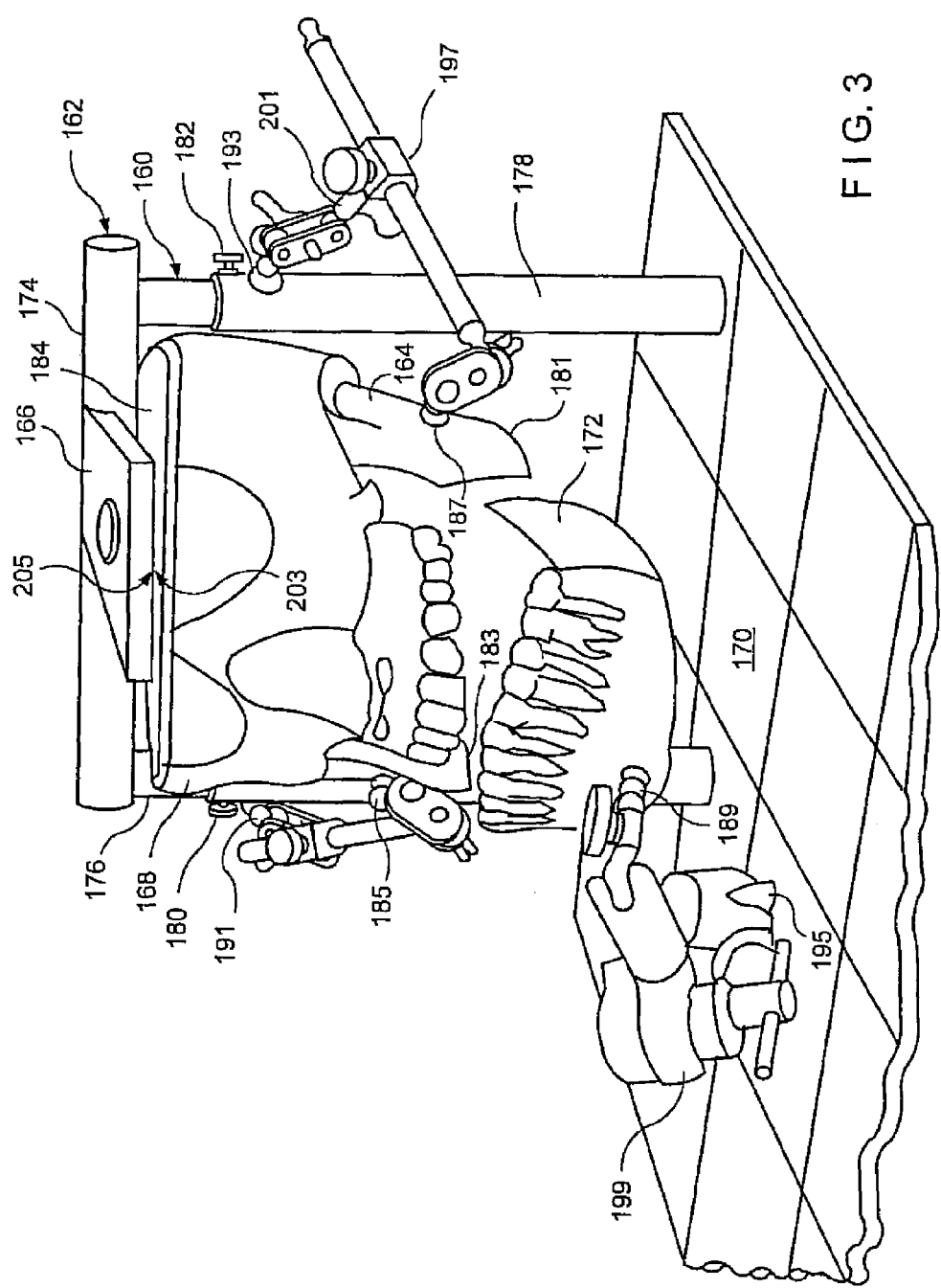
FIG. 3 is a perspective view of the second embodiment of the craniofacial anatomic surgical simulator of this invention utilising transfer assemblies to hold segments of the stereolithographic model.

Referring now to FIG. 3, a second embodiment of the craniofacial anatomic surgical simulator (CAS) is shown and is now described. The CAS device is referred to generally by the reference designator 160. In this embodiment, similar parts to those of the first embodiment are referred to by reference designators 100 units higher than a similar part in the first embodiment.

The CAS device 160 provides a framework 162 for accommodating the stereolithographic model 164. The framework 162 is constructed with an upper mounting plate or extension arm 166. Optionally, the mounting plate 166 is constructed to include a universal swivel joint (not shown) for freely adjusting the same. The upper mounting plate 166 attaches the craniomaxillary portion 168 of the stereolithographic model 164. The framework 162 further includes a base mounting plate 170 for attaching the mandibular portion or mandible 172 of the stereolithographic model 164.

The framework 162 of the CAS 160 further comprises a crossbar or strut 174 to which the upper mounting plate 166 is connected. Adjustable posts 176 and 178 are held by retaining elements 180 and 182 to maintain upper mounting plate 166 at the selected elevation.

As previously mentioned, the stereolithographic model 164 consists of two basic parts, namely, the craniomaxillary portion 168 and mandible 172 is modified slightly differently from that of the first embodiment. Here, at each ramus segment 181 and 183, corresponding male attachment node or ramus connector 185 and 187 is emplaced. Similarly an attachment node or mandible connector 189 is emplaced on mandible 172. For easy management of the stereolithographic model 164, the framework 162 is constructed with a male attachment node or column connector 191 and 193 on each adjustable post 176 and 178, respectively, and at least one base connector 195 on base 170. Between ramus connector 185 and column connector 191, a manipulator or transfer device 197 (such as Transfer Set Model 050-150 of SAM—Präzisionstechnik Gmbh, Gauting, Germany or equivalent) holds the ramus segment 181 (which has been separated from mandible 172).

As shown in FIG. 3, a manipulator or transfer device 199 (such as Axiomatic Transfer Fork Assembly Model 050-155 of SAM—Präzisionstechnik Gmbh, Gauting, Germany or equivalent) holds the mandibular segment 172 between base connector 195 and mandibular connector 189. Completing the mounting arrangement for the model 164, the ramus segment 183 in a manner analogous to segment 181, is held by a transfer device 201 between ramus connector 187 and column connector 193.

The stereolithographic model 164 is truncated by having the uppermost cranial portion removed and replace by a cranial mounting plate 184. In this embodiment the midlines of the cranial mounting plate 184 and the upper mounting plate 166 form a reference means with, for example, the midline 203 of cranial mounting plate 184 being raised and midline 205 of upper mounting plate 166 being indented. Thus, upon mounting, midline 203 interengages with midline 205 resulting in the positive indexing of stereolithographic model 164 on framework 162.

Referring now to FIGS. 4 and 5, the craniofacial anatomic simulator 160 of this invention includes a cephalometer consisting of an array of three digital calipers for providing cephalometric data. The digital calipers measure along an x-axis 207 or a substantially horizontal line parallel to the front edge of the base 170. Thus, lateral position digital caliper 209 mounted on scale bar 211 provides the right-to-left data. The digital calipers also measure along y-axis 213 or a substantially vertical line parallel to the longitudinal axis of column 215 and measures elevation with reference to an origin such as base 170. Thus, elevation position digital caliper 217 mounted on column 215 provides the up-and-down data. The z-axis 219 runs horizontally and normal to an xy-plane and measurement in this direction provides depth or front-to-back position. The depth digital caliper 221 also mounted on column 215 provides the front-to-back data. Where a depth location is behind protruding front-to-back stereolithographic material, the depth caliper 221 is equipped with an offset head 223 with an arm 225 to reach behind the interfering stereolithographic material and the known offset is accounted for when entering the data in the database.

The cephalometric data collected as described in the preceding paragraph is, for distraction osteogenesis, gathered on two occasions, namely: (1) at start up-to register the model condition which represents the actual pre-operative patient; and, (2) at reconfiguration-to register the re-assembled model condition which represents the clinically selected post-operative condition. When any predetermined position of a portion of the stereolithographic model is to be replicated, the clinician using the cephalometer hereof can gather a data set—elevation, depth and lateral position—for any three selected points thereon and later replicate the position using the gathered data. For other orthognathic craniofacial or dental procedures, data gathering may represent intermediate points according to the clinician's plans. It is within the contemplation of the present invention that the data collected can be deposited directly into a computerized database with associated graphic modelling.

Referring again to FIG. 4, another mounting arrangement for mandibular portion 172 is shown. A mandibular attachment column 227 is erected on mounting plate 170 with a vertically adjustable mandibular positioning rod 229 reciprocally positionable along column 227. In prior articulators, the mandibular mounting was fixed and mandibular movement was approximated by changing the position of the craniomaxillary portion 168.

While a three-dimensional cephalometry is obtained herein using three digital calipers for height, depth and lateral position, it is within the contemplation of this invention that the same could be accomplished from a radial track and a similar mast with only two digital calipers. Because many varying and different embodiments may be made within the scope of the inventive concept herein taught and because many modification may be made in the embodiments herein detailed in accordance with the descriptive requirements of the law, it is to be understood that the details herein are to be interpreted as illustrative and not in a limiting sense.

What is claimed is:

1. An apparatus for mounting craniofacial anatomic components used in simulation of dental and surgical procedures comprising:
   a fixed base;
   a pair of columns arising from said base, said columns being of adjustable height;
   a mounting plate cantilevered from said columns, said mounting plate adapted to receive a truncated craniomaxillary portion thereon, said mounting plate with said truncated craniomaxillary portion depending therefrom being raised and lowered upon adjustment of said columns;
   a movable base disposed on said fixed base, said movable base adapted to receive a mandibular portion thereon, said movable base with said mandibular portion thereon, positionable with three degrees of freedom in relation to said truncated craniomaxillary portion; and,
   a cephalometer disposed on said base providing locational data for any point on said craniomaxillary portion and said mandibular portion, said cephalometer further comprises;
      a column affixed to said base arising vertically therefrom;
      an elevation position digital caliper movable disposed on said column for upward and downward positioning, said elevation position digital caliper providing a numeric readout representing elevation;
      a depth digital caliper movably disposed on said column for inward and outward positioning, said depth digital caliper providing a numeric readout representing depth;
      a scale bar disposed on said base parallel to the front edge thereof and providing a track thereacross; and,
      a lateral position digital caliper movably disposed on said scale bar for lateral positioning therealong said lateral position digital caliper providing a numeric readout representing right-to-left position;
   whereby, upon simulation, said anatomic components are moved to post-operative positions providing requisite surgical planning.

2. An apparatus as described in claim 1 wherein said depth digital caliper has an offset head to reach behind interfering anatomic components.

3. An apparatus as described in claim 1 wherein any three data sets of said cephalometer of said truncated craniomaxillary portion defines the mounting thereof and enables the replication of the mounting of said truncated craniomaxillary portion.

4. An apparatus as described in claim 1 wherein any three data sets of said cephalometer of said mandibular portion defines the mounting thereof and enables the replication of the mounting of said mandibular portion.

5. A craniofacial anatomic simulator comprising:
a mounting apparatus for a stereolithographic model, in turn, comprising:
a fixed base;
a pair of columns arising from said base, said columns being of adjustable height;
a mounting plate cantilevered from said columns, said mounting plate adapted to receive a truncated craniomaxillary portion thereon, said mounting plate with said truncated craniomaxillary portion depending therefrom being raised and lowered upon adjustment of said columns; and,
manipulator means disposed on said fixed base, adapted to receive a mandibular portion thereon, said manipulator means with said mandibular portion thereon positionable with three degrees of freedom in relation to said truncated craniomaxillary portion;
a medical model fabricated using computerized tomographic techniques from digitized data, said medical model, in turn, comprising:
a truncated craniomaxillary portion having the uppermost region removed leaving an opening thereinto;
a cranial attachment plate at said opening of said truncated craniomaxillary portion, said cranial attachment plate affixed to said mounting plate of said mounting apparatus;
a mandibular portion; and,
a glenoid fossae with a simulated soft tissue component therein attached to said truncated craniomaxillary portion; and,
a simulated masseteric sling having elastic material extending from the zygomatic arch of said medical model to said mandible of said medical model;
said simulated soft tissue of said glenoid fossae and said simulated masseteric sling are constructed to replicate the translational and rotational components of the excursive movement of a temporomandubular joint;
said mounting apparatus further comprises a cephalometer disposed on said fixed base providing locational data for any point on said craniomaxillary portion and said mandibular portion, said cephalometer further comprises:
a column affixed to said base arising vertically therefrom;
an elevation position digital caliper movably disposed on said column for upward and downward positioning, said elevation position digital caliper providing a numeric readout representing elevation;
a depth digital caliper movably disposed on said column for inward and outward positioning, said depth digital caliper providing a numeric readout representing depth;
a scale bar disposed on said base parallel to the front edge thereof and providing a track thereacross; and,
a lateral position digital caliper movably disposed on said scale bar for lateral positioning therealong, said lateral position digital caliper providing a numeric readout representing right-to-left position;
whereby upon registering a readout from said elevation position digital caliper, from said depth digital caliper, and from said lateral position digital caliper a discrete cephalometric datum is obtained.

6. An apparatus as described in claim 5 wherein said depth digital caliper has an offset head to reach behind interfering anatomic components.

7. An apparatus as described in claim 5 wherein any three data sets of said cephalometer of said truncated craniomaxillary portion defines the mounting thereof and enables the replication of the mounting of said truncated craniomaxillary portion.

8. An apparatus as described in claim 5 wherein any three data sets of said cephalometer of said mandibular portion defines the mounting thereof and enables the replication of the mounting of said mandibular portion.

9. An apparatus as described in claim 5 wherein said craniomaxillary portion is indexed to said mounting plate using cranial midline data and inscribing the midline on said cranial attachment plate, said cranial midline being raised and a midline channel being impressed in said mounting plate;
whereby, upon said craniomaxillary portion being mounted on said cranial attachment plate and engaging said cranial midline, said craniomaxillary portion is indexed to said mounting plate.

10. An apparatus as described in claim 5 further comprising:
a mandibular attachment column disposed on said fixed base and arising substantially vertically therefrom; and,
a mandibular positioning rod extending between said mandibular attachment column and said mandibular portion and having said mandibular portion fixedly mounted thereto, said mandibular positioning rod being reciprocally movable along said mandibular attachment column.

11. A medical model for simulating craniofacial surgery fabricated using computerized tomography from digitized data, said medical model comprising:
a truncated craniomaxillary portion having the uppermost region removed leaving an opening thereinto;
a cranial attachment plate at the said opening of said truncated craniomaxillary portion, said cranial attachment plate adapted for mounting said medical model to a surgical simulator;
a glenoid fossae with simulated soft tissue component thereon attached to said truncated craniomaxillary portion; and,
a mandible with the condyle thereof disposed in said glenoid fossae of said temporomandibular joint; and,
a simulated masseteric sling having elastic material extending from the zygomatic arch of said medical model to said mandible of said medical model;
whereby said medical model is mountable in a craniofacial anatomic surgical simulator to demonstrate pre-operative conditions and to simulate surgical procedures.

12. A medical model as described in claim 11 wherein said simulated soft tissue of said glenoid fossae and said simulated masseteric sling are constructed to replicate the translational and rotational components of the excursive movement of a temporomandibular joint.

13. A medical model as described in claim 11 wherein said medical model is a stereolithographic device.

14. A medical model as described in claim 11 wherein said craniomaxillary portion is indexed to said mounting plate using cranial midline data and inscribing the midline on said cranial attachment plate, said cranial midline being raised and a midline channel being impresses in said mounting plate;
whereby, upon said craniomaxillary portion being mounted on said cranial attachment plate and engaging said cranial midline, said craniomaxillary portion is indexed to said mounting plate.

* * * * *